US011210599B2

(12) United States Patent
Nishikawa et al.

(10) Patent No.: US 11,210,599 B2
(45) Date of Patent: Dec. 28, 2021

(54) INFORMATION PROCESSING APPARATUS AND METHOD

(71) Applicant: FUJITSU LIMITED, Kawasaki (JP)

(72) Inventors: Ryusuke Nishikawa, Kawasaki (JP); Yoshifumi Ujibashi, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 1084 days.

(21) Appl. No.: 15/808,924

(22) Filed: Nov. 10, 2017

(65) Prior Publication Data

US 2018/0181874 A1    Jun. 28, 2018

(30) Foreign Application Priority Data

Dec. 28, 2016 (JP) .............................. JP2016-256723

(51) Int. Cl.
*G06N 7/00* (2006.01)
*G06F 17/18* (2006.01)
*G16B 40/00* (2019.01)

(52) U.S. Cl.
CPC ............. *G06N 7/005* (2013.01); *G06F 17/18* (2013.01); *G16B 40/00* (2019.02)

(58) Field of Classification Search
CPC .......... G06F 17/18; G06N 7/005; G16B 40/00
See application file for complete search history.

(56) References Cited

U.S. PATENT DOCUMENTS

| | | | | |
|---|---|---|---|---|
| 2002/0178410 A1* | 11/2002 | Haitsma | ................ | G06F 16/785 714/709 |
| 2009/0112850 A1 | 4/2009 | Toyoda et al. | | |
| 2010/0124743 A1* | 5/2010 | Nagaoka | .......... | C12Q 2545/114 435/6.14 |
| 2010/0274893 A1* | 10/2010 | Abdelal | ................. | H04L 47/10 709/224 |
| 2013/0073065 A1* | 3/2013 | Chen | ..................... | G10L 19/018 700/94 |
| 2013/0157272 A1* | 6/2013 | Adai | .................... | C12Q 1/6886 435/6.12 |
| 2013/0191049 A1* | 7/2013 | Sales Casals | .......... | G01R 31/12 702/58 |
| 2014/0155411 A1* | 6/2014 | Ochsner | .............. | A61K 31/496 514/254.11 |

(Continued)

FOREIGN PATENT DOCUMENTS

WO    2007126088    11/2007

OTHER PUBLICATIONS

Aika Terada et al., "High-speed Westfall-Young permutation procedure for genome-wide association studies", ACM-BCB Sep. 9-12, 2015, pp. 17 to 26 (10 pages).

(Continued)

*Primary Examiner* — Tuan C Dao
(74) *Attorney, Agent, or Firm* — Fujitsu Patent Center

(57) ABSTRACT

An information processing apparatus is disclosed. A processor acquires an upper limit and a lower limit of a probability of a false positive for each of multiple tests based on data-after-aggregation pertinent to a presence or absence of a specific event occurrence acquired by multiple testing, and sets a value from multiple upper limits being acquired. The processor calculates the probability of the false positive with respect to each of tests having lower limits less than the value, and acquires a set of probabilities of the false positive.

7 Claims, 13 Drawing Sheets

(56) References Cited

U.S. PATENT DOCUMENTS

2014/0336280 A1* 11/2014 Albitar ................ C12Q 1/6886
514/789
2017/0115301 A1* 4/2017 Hall ...................... C07K 16/18

OTHER PUBLICATIONS

Matthew Skala, "Hypergeometric tail inequalities: ending the insanity", Nov. 26, 2013, pp. 1 to 5 (5 pages).

* cited by examiner

|  | case | control | total |
|---|---|---|---|
| MUTATED | $n$ | $x - n$ | $x$ |
| NO MUTATION | $N_c - n$ | $N_t - x - N_c + n$ | $N_t - x$ |
| total | $N_c$ | $N_t - N_c$ | $N_t$ |

ONE TEST

⬇

PROBABILITY OF
FALSE POSITIVES: 5%

TEN TESTS

⬇

$1 - 0.95^{10} = 0.4$  40%

TWO INDEPENDENT
TESTS

TWO DEPENDENT
TESTS

FIG.9

| ID | PRESENCE OR ABSENCE OF SPECIFIC EVENT OCCURRENCE | 42 DATA-BEFORE-AGGREGATION ||||
|---|---|---|---|---|---|
| | | ATTRIBUTE_1 | ATTRIBUTE_2 | ... | ATTRIBUTE_m |
| 1 | 0 | 1 | 1 | | 0 |
| 2 | 1 | 0 | 1 | | 0 |
| 3 | 1 | 1 | 0 | | 1 |
| 4 | 0 | 0 | 0 | | 0 |
| ... | ... | ... | ... | | ... |

FIG.10

| OBSERVED FREQUENCY $n$ | MARGINAL FREQUENCY $x$ | MARGINAL FREQUENCY $N_c$ | MARGINAL FREQUENCY $N_t$ |
|---|---|---|---|
| 21 | 43 | 45 | 91 |
| 6 | 12 | 44 | 89 |
| ... | ... | ... | ... |
|  |  |  |  |

43 DATA-AFTER-AGGREGATION

FIG.11

44 MINIMUM p-VALUE TABLE

| MINIMUM p-VALUE | ... |
|---|---|
| 0.0004 | ... |
| 0.0006 | ... |
| 0.0007 | ... |
| ... | ... |

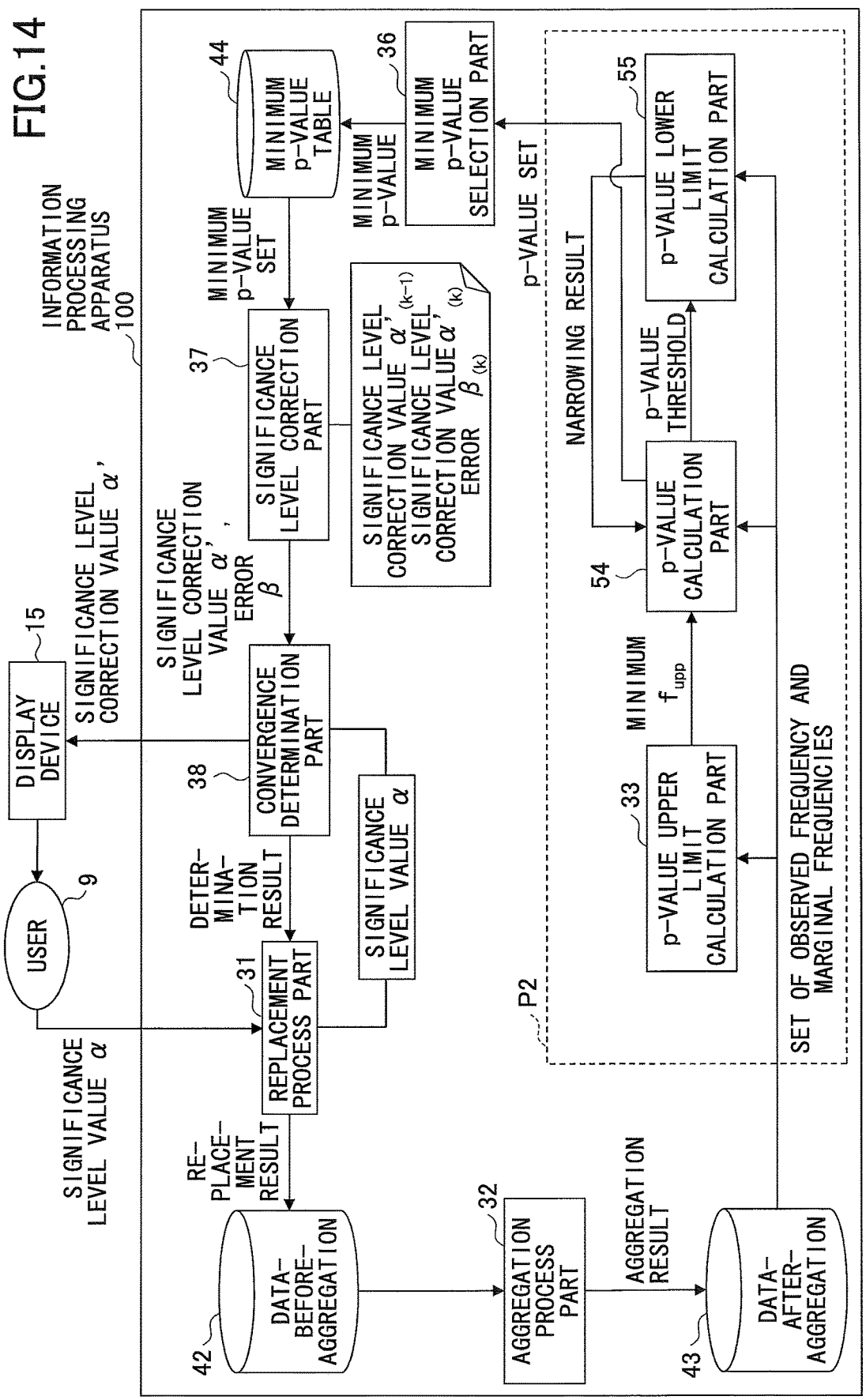

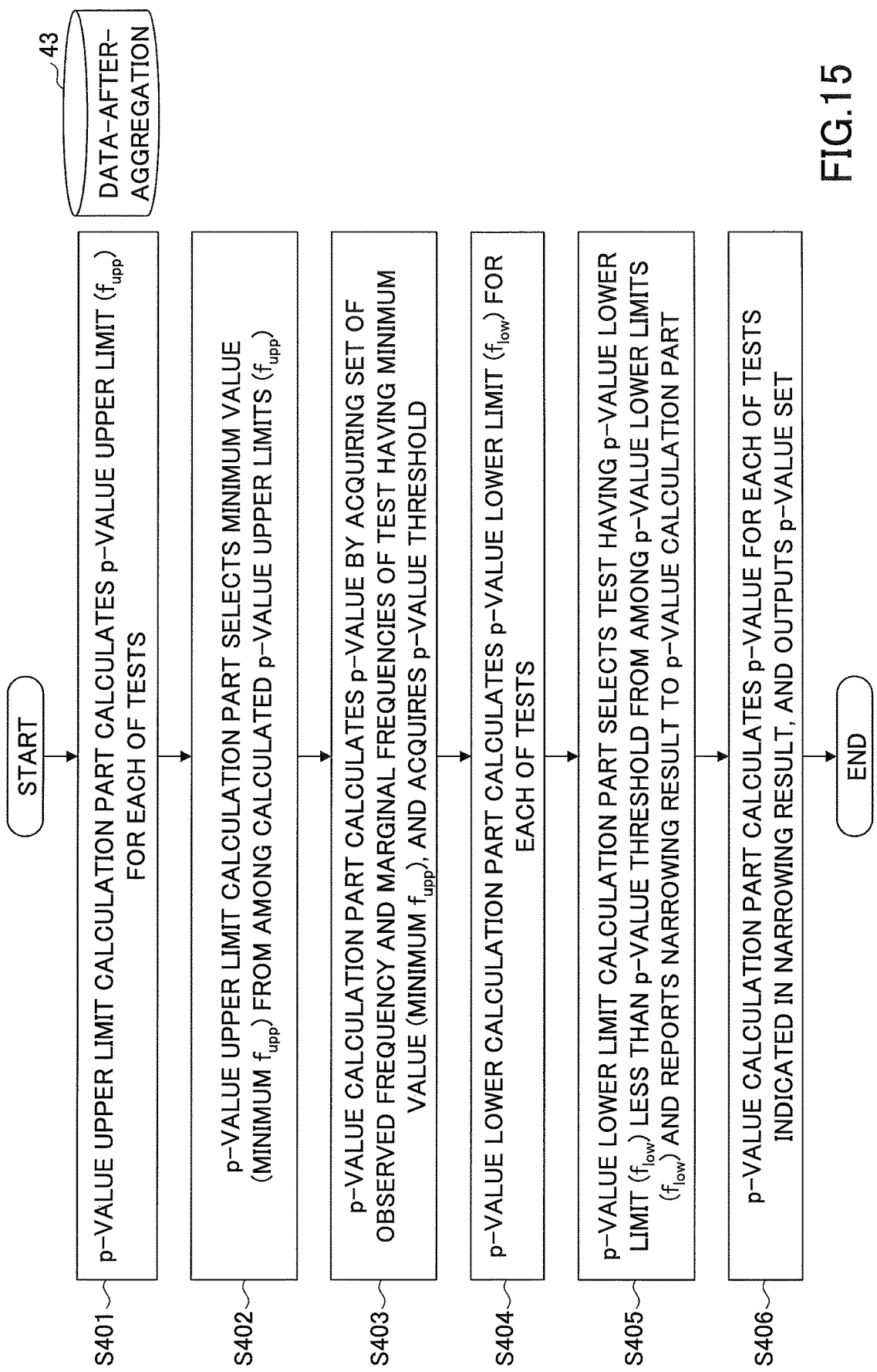

INFORMATION PROCESSING APPARATUS AND METHOD

CROSS-REFERENCE TO RELATED APPLICATIONS

This application is based upon and claims the benefit of priority of the prior Japanese Patent Application No. 2016-256723, filed on Dec. 28, 2016, the entire contents of which are incorporated herein by reference.

FIELD

The embodiment discussed herein is related to an information processing apparatus, a computer-readable recording medium storing an information processing program, and an information processing method.

BACKGROUND

In a field of statistics, hypothesis testing is frequently used. In the hypothesis testing, certain hypotheses are made and examined based on probabilities.

Regarding searches of biological items in biology, a chemistry, and the like, a technology is presented in that references are defined by using documents describing a phenotype and a genotype for each of patients in an exploratory research of a disease-related gene polymorphism, in which each of the bio items is defined by the genotype, and words related to the phenotype are used as keywords. By this technology, it becomes possible to search the genotype most correlated with the phenotype in order of a significance probability.

PATENT DOCUMENTS

[Patent Document 1]
International Publication Pamphlet No. WO2007/126088

Non-Patent Documents

[Non-Patent Document 1]
Terada, Kim and Sese, "High-speed Westfall-Young permutation procedure for genome-wide association studies," ACM-BCB 2015
[Non-Patent Document 2]
Skala, "Hypergeometric tail inequalities: ending the insanity," arXiv 1311.5939

SUMMARY

According to one aspect of the embodiments, there is provided an information processing apparatus including a memory; and a processor coupled to the memory and the processor configured to acquire an upper limit and a lower limit of a probability of a false positive for each of multiple tests based on data-after-aggregation pertinent to a presence or absence of a specific event occurrence acquired by a multiple testing; set a value from multiple upper limits being acquired; calculate the probability of the false positive with respect to each of tests having lower limits less than the value; and acquire a set of probabilities of the false positive.

According to other aspects of the embodiments, a computer-readable recording medium storing an information processing program, and an information processing method are provided.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 9 is a diagram illustrating a configuration example of data-before-aggregation;
FIG. 10 is a diagram illustrating a configuration example of data-after-aggregation;
FIG. 11 is a diagram illustrating a configuration example of a minimum p-value table;
FIG. 14 is a diagram illustrating a second example of the functional configuration of the information processing apparatus in the embodiment;
and
FIG. 15 is a flowchart for explaining the narrowing process using the inequality in the second example of the functional configuration in FIG. 14.

DESCRIPTION OF EMBODIMENTS

In a hypothesis testing, a probability level for determining whether to reject a certain hypothesis is called "significance level" (indicated by $\alpha$). It is referred to as a false positive or a type I error (an error of a first kind) such that the false positive is inherently negative. A case of $\alpha=0.05$ means that a probability, in which a false positive occurs, is 5%.

In hypothesis testing, by calculating the probability of the false positive (called "p-value") from given data, a statistical significance is determined based on whether the p-value is greater than the significance level. For instance, regarding a hypothesis "there is no significant difference in the proportion of men and women who are dieting", the hypothesis is discarded when the p value is lower than the significance level. That is, if $p<0.05$, a probability of happening by chance is considered to be 5% or less. Hence, it is concluded that the significant difference is present rather than coincidence.

However, in multiple testing in which a plurality of hypothesis tests occur simultaneously, a calculation amount for calculating this p-value becomes an enormously large amount. In the above described related technology for precisely defining search targets, the calculation amount of the p-value is not reduced.

In an aspect of an embodiment described below, an object is to reduce the calculation amount for the probability of the false positive in the multiple testing.

A preferred embodiment of the present invention will be described with reference to the accompanying drawings. First, the hypothesis testing will be described. Fisher's exact test (hereinafter, simply called "Fisher's test") is well known in a field of statistics as a method for conducting the hypothesis testing of data, in which each of two groups is classified into two categories.

As an example, Fisher's test is used in a case of testing a hypothesis "there is no significant difference in ratio for two categories, dieting persons who are dieting and persons who are not between two groups: men and women." With respect to this hypothesis, a statistical significance is determined based on whether the p-value is greater than the significance level.

In the following, Fisher's test will be briefly described. As an example, persons are classified into two groups: person who have a certain illness (case) and person who do not have the illness (control). Moreover, in each of these two groups, persons are classified into persons with mutations and persons without mutations, regarding bases (elements responsible for DNA genetic information). Such a classification is represented by a cross tabulation table as depicted in FIG. 1.

Figures 1, 2:
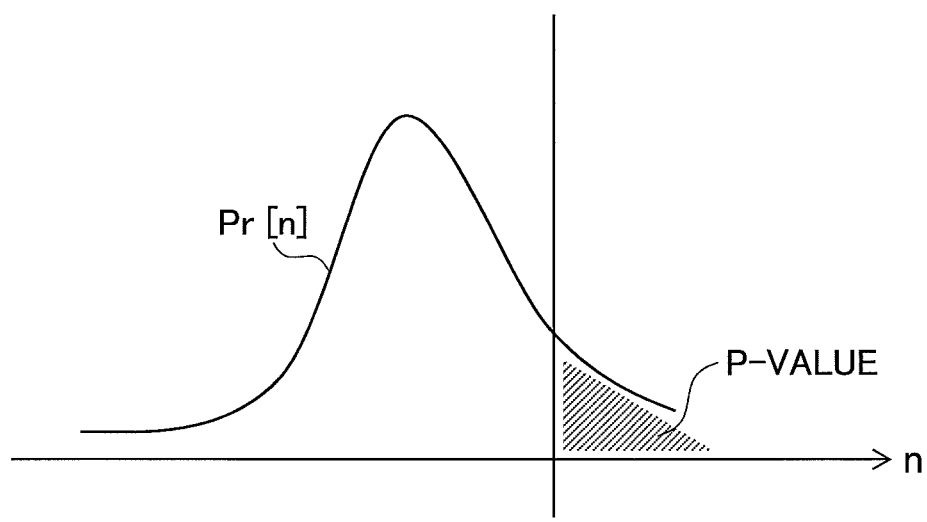
FIG. 1 is a diagram illustrating an example of a cross tabulation table.
FIG. 2 is a diagram for explaining a probability function and a p-value.

FIG. 1 is a diagram illustrating an example of the cross tabulation table. In the cross tabulation table illustrated in FIG. 1, n denotes a number of people with onset of disease and mutation, $\chi$ denotes a total number of people with mutation, $N_c$ denotes a total number of people with onset, and $N_t$ denotes a total number of people in the cross tabulation table (that is, a test number).

In the cross tabulation table, n, $\chi-n$, $N_c-n$, and $N_t-\chi-N_c+n$ are called "observed frequencies". Also, $\chi$, $N_t-\chi$, $N_c$, $N_t-N_c$, and $N_t$ correspond to "marginal frequencies". As described above, a presence or absence of the onset of a specific disease is exemplified. Alternatively, such a cross tabulation table may be used for a presence or absence of product purchase or the like.

Based on this cross tabulation table, a calculation method of the p-value indicating the probability of the false positive will be described. With respect to the cross tabulation table depicted in FIG. 1, the p-value is calculated by following Formula 1 and Formula 2. A relationship between a probability function Pr obtained by Formula 1 and the p-value obtained by Formula 2 is illustrated in FIG. 2.

First, in the cross tabulation table in FIG. 1, in a state in which the marginal frequencies are given, the probability function Pr, for which the number of people with the onset and the mutation is indicated by n, is represented by Formula 1;

$$Pr(n; x, N_c, N_t) = \frac{\binom{x}{n}\binom{N_t-x}{N_c-n}}{\binom{N_t}{N_c}}.$$  [Formula 1]

In FIG. 2, the probability function Pr(n; $\chi$, $N_c$, $N_t$) is simply expressed by Pr[n]. According to the probability function Pr, the p-value of Fisher's test is represented by Formula 2;

$$p(n; x, N_c, N_t) = \sum_{i=n}^{x} Pr(i).$$  [Formula 2]

In FIG. 2, a shaded area indicates an area of the probability of occurring by chance. As an example, 5% is set. In this case, when the p-value is less than or equal to 5%, it is indicated that there is a significant difference, and not by chance.

In the above, one hypothesis test is described. A case in which multiple hypothesis tests simultaneously occur is called "multiple testing." For instance, in order to specify a base (element responsible for DNA genetic information), the hypothesis testing is repeated multiple times due to a large number of bases.

Figure 3A:
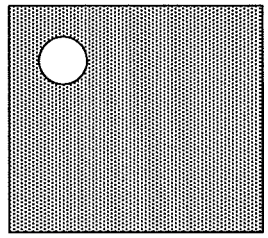
FIG. 3A and FIG. 3B are diagrams for explaining a case in which a type I error occurs in multiple testing.
Figure 3B:
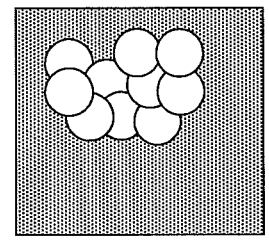

FIG. 3A and FIG. 3B are diagrams for explaining a case in which a type I error occurs in the multiple testing. In FIG. 3A and FIG. 3B, one round shape represents the probability of a false positive occurring in one test. FIG. 3A depicts a result example of the one test. In a case in which the significant level a is 5%, the probability, in which a false positive occurs, is 5% in FIG. 3A.

FIG. 3B depicts a result example of ten tests. In this case, 0.4 is acquired by calculating $1-0.95^{10}$. That is, the probability, in which the false positive occurs, is at least 40% for one set of tests. As described above, in the multiple testing, the more the number of tests, the higher probability a type I error occurs.

As a method for correcting the significance level to reduce such a high probability of the false positive, various multiple testing corrections are presented. As such multiple testing corrections, Bonferroni's method, Holm's method, Tarone's method, a permutation method (which may be called "Westfall-Young's method"), and the like have been known.

Figure 4A:
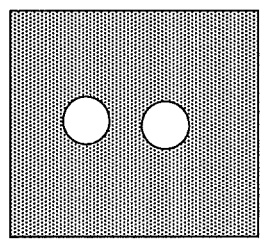
FIG. 4A and FIG. 4B are diagrams for explaining an example of dependencies among a plurality of tests.
Figure 4B:
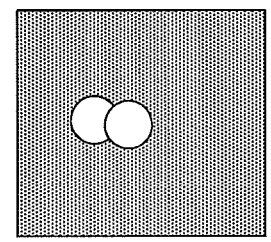

In the following, the permutation method (Westfall-Young's method) will be briefly described. The permutation method enables treatment of dependencies among a plurality of tests. FIG. 4A and FIG. 4B are diagrams for explaining an example of the dependencies among the plurality of the tests. In FIG. 4A and FIG. 4B, the probability of the false positive caused by one test is represented by one round shape in the same manner described above.

FIG. 4A illustrates an example of two independent tests. FIG. 4B illustrates an example of two dependent tests. The permutation method enables treatment of dependencies among multiple tests having dependencies, as depicted in FIG. 4B.

The permutation method uses a numerical simulation (hereinafter, simply called "simulation"), and repeatedly conducts the following process until a calculation is converged.

randomly arrange presence or absence of a specific event occurrence in given data (data-before-aggregation 42 (FIG. 9)) (permutation), create a cross tabulation table, and calculate a p-value.
  select a minimum p-value from all tests.
  numerically calculate a probability distribution of the minimum p-values based on a set of the minimum p-values as acquired for each simulation.
  determine a correction value of the multiple testing correction based on the probability distribution of the minimum p-values.

Figure 5:
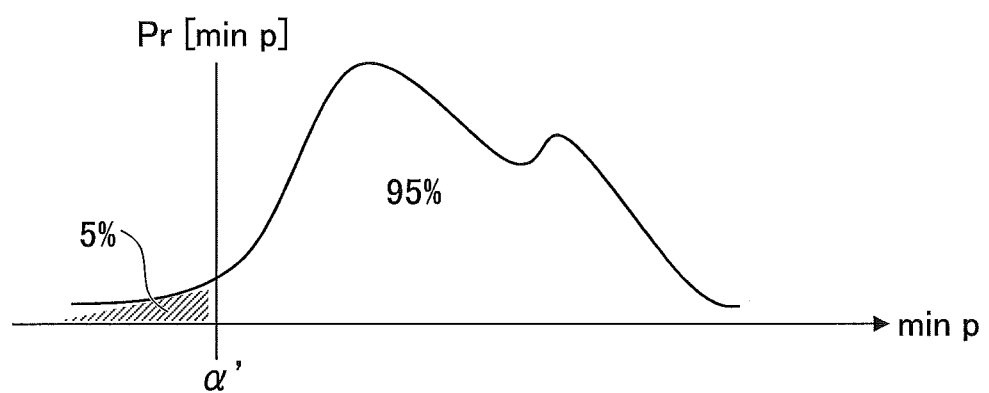
FIG. 5 is a diagram illustrating an example of a probability distribution of minimum p-values.

FIG. 5 is a diagram illustrating an example of the probability distribution of minimum p-values. In FIG. 5, a probability distribution Pr[min p] of minimum p-values, which is numerically acquired, is depicted, and the significance level (significance level correction value α'), which is obtained from the probability distribution Pr[min p] of minimum p-values, is indicated.

Referring to FIG. 5, a probability of the minimum p-value being less than the significance level correction value α' is 5%. That is, a probability of the false positive occurring for at least one test in the multiple testing is 5%.

The above described Fisher's test is frequently used; however, due to a large calculation amount for calculating the p-value, the calculation takes a large amount of time. Especially in Formula 1, when the marginal frequency N of the cross tabulation table is increased, a calculation amount of a product becomes enormous. In the permutation method for correcting the multiple testing, since the p-value is repeatedly calculated, an increase in a calculation cost of p-value leads to an increase in a calculation cost of the entire permutation method.

Thus, as a method for calculating the p-value of the Fisher's test at a high speed, a method using a lookup table (Non-Patent Document 1) is known. In this method, a once calculated p-value is stored in the lookup table. In a case of calculating the p-value for the same argument values (n, χ, N, $N_t$), the p-value is searched in the lookup table.

As an example, in a case of conducting tests for numerous bases that may be associated with a disease, the observation frequency n and the marginal frequency χ take different values for each of the bases; however, the marginal frequencies $N_c$ and $N_t$ take common values, respectively, for all bases. Therefore, the lookup table may retain a combination of the observation frequency n and the marginal frequency χ.

As described above, by searching through the lookup table, it is possible to obtain the p-value at a higher speed than a case of directly calculating the p-value.

However, in a case of processing data containing missing values, values of the marginal frequencies $N_c$ and $N_t$ become different for each of the bases as well as the observation frequency n and the marginal frequency χ, and a number of combinations of the argument values (n, χ, $N_c$, $N_t$) becomes numerous. Since there is almost no opportunity of calculating again with a previously calculated p-value again, a process for searching the lookup table is rarely conducted. That is, it becomes difficult to realize a high speed process.

Accordingly, in order to reduce the calculation amount for acquiring the p-value, the permutation method is further examined. First, a method, which is conceivable for a person with knowledge concerning permutations, will be examined.

The permutation method does not need the p-values for all tests, but needs the minimum p-value alone at each permutation. Therefore, in order to reduce the calculation cost, a method is considered to narrow down tests to be candidates (test candidates), which may have the minimum p-value and to calculate the p-value for the candidates alone.

As an index representing a statistical bias of the cross tabulation table (FIG. 1), an Odds Ratio (OR) is frequently used. "OR" is expressed by the following Formula 3:

$$OR = \frac{n/(x-n)}{(N_c - n)/(N_t - x - N_c + n)}. \quad \text{[Formula 3]}$$

A calculation cost of "OR" is sufficiently less than a cost of a p-value calculation of Fisher's test. Accordingly, it may be considered that "OR" is first calculated for all tests, and then, the tests are narrowed down to tests having greater "OR" values as candidates from which the minimum p-value may be obtained.

In this method, since there is arbitrariness in determining a threshold of "OR" at a time of narrowing down the tests, the calculation cost and a result are varied depending on an experience of an analyst. Since a magnitude relation of "OR" does not always correspond to that of the p-value of Fisher's test, the p-value is not precisely acquired depending on a method for determining the threshold. As a result, an accuracy of the significance level correction may be degraded.

In the embodiment as described below, in acquiring an accurate p-value, the calculation amount for obtaining the p-value is reduced without degrading the accuracy of the multiple testing.

In a method for narrowing down the tests using "OR" described above, there may be a case in which the minimum p-value is not accurately acquired. In order to solve this problem, the inventors of the present Patent Application have found a method using a function with a clear relationship to the p-value (Formula 2) of Fisher's test. According to the method of the inventors, by calculating an upper limit and a lower limit of the p-value, the p-values are precisely narrowed down. Thus, it is possible to acquire a correction value of the significant level a (significant level correction value α') without degrading its accuracy.

First, an effective inequality giving the upper limit of the p-value is known (Non-Patent Document 2). In the multiple testing, "Effective" means that a difference between the accurate p-value and the upper limit is small and that the calculation amount for acquiring the upper limit is sufficiently less than that for acquiring the p-value.

As described above, the effective inequality (Formula 6) for acquiring the upper limit of the p-value has been known; however, an effective inequality giving the lower limit of the p-value is not known. Since the inventors are familiar with a nature of a probability density function (Formula 1) of a hypergeometric distribution and the permutation method both used for the p-value calculation, the inventors have found a method as described below.

First, the inventors have focused on a fact that only a tail of the probability density function (Formula 1) of the hypergeometric distribution is referred to in order to calculate the minimum p-value used for the permutation method. That is, the inventors have focused on a nature in which the tail exponentially decreases, and invented a lower limit expression in which the p-value originally given by a summation of probability density functions is approximately given by one probability density function alone as a term. Moreover, the inventors have invented a lower limit expression (Formula 5) by applying Stirling's formula to the probability density function of the hypergeometric distribution and transforming it to a lower limit formula having a lesser calculation amount.

In the following, a method for narrowing down the tests using the lower limit expression found by the inventors will be described. The following inequality is used with respect to the probability function Pr defined by Formula 2:

$$f_{low}(n,x,N_c,N) \le \log p(n;x,N_c,N) \le f_{upp}(n,x,N_c,N). \quad \text{[Formula 4]}$$

Also, $f_{low}$ and $f_{upp}$ are defined by Formula 5 and Formula 6:

$$f_{low}(n, x, N_c, N_t) = -x[p_A \log p_A + (1-p_A) \log(1-p_A)] - \quad \text{[Formula 5]}$$
$$(N_t - x)[p_C \log p_C + (1-p_C) \log(1-p_C)] +$$
$$N_t[p_B \log p_B + (1-p_B) \log(1-p_B)],$$
$$p_A = \frac{n}{x}, \; p_B = \frac{N_c}{N_t}, \; p_C = \frac{N_c - n}{N_t - x},$$
and $$f_{upp}(n, x, N_c, N_t) := -2t^2 N_c, \quad \text{[Formula 6]}$$
$$\text{where } n = \left(\frac{x}{N_t} + t\right) N_c \text{ with } t \geq 0.$$

Next, a transformation of expressions in order to acquire Formula 4 from Formula 2 will be described. The following Formula 7 related to the p-value of Fisher's test expressed by Formula 2 is known due to Non-Patent Document 2:

$$p(n; x, N_c, N_t) \leq e^{-2t^2 N_c}, \text{ where } n = \left(\frac{x}{N_t} + t\right) N_c \text{ with } t \geq 0. \quad \text{[Formula 7]}$$

By referring to Formula 2, the following inequality is satisfied:

$$p(n;x,N_c,N_t) \geq Pr[n;x,N_c,N_t] \quad \text{[Formula 8]}$$

By referring to Formula 7 and Formula 8, taking logarithms, the following Formula 9 is satisfied:

$$\log(Pr[n;x,N_c,N_t]) \leq \log(p) \leq -2t^2 N_c. \quad \text{[Formula 9]}$$

With respect to a leftmost side of Formula 9, Stirling's formula, $$(n+\tfrac{1}{2})\log n - n + \log\sqrt{2\pi} \leq \log n! \leq (n+\tfrac{1}{2})\log n - n + 1, \quad \text{[Formula 10]}$$

is used, and then, Formula 11, $$\log(Pr(n, x, N_c, N_t)) \geq \quad \text{[Formula 11]}$$
$$-x[p_A \log p_A + (1-p_A) \log(1-p_A)] -$$
$$(N_t - x)[p_C \log p_C + (1-p_C) \log(1-p_C)] +$$
$$N_t[p_B \log p_B + (1-p_B) \log(1-p_B)],$$
$$p_A = \frac{n}{x}, \; p_B = \frac{N_c}{N_t}, \; p_C = \frac{N_c - n}{N_t - x},,$$

is acquired. Therefore, Formula 4 is obtained by Formula 10 and Formula 11.

In the method for narrowing down the tests in the embodiment, the function $f_{upp}$ is calculated for each of the tests and a minimum value of the function $f_{upp}$ is acquired. Hereinafter, the minimum value of the function $f_{upp}$ is called "minimum $f_{upp}$." Next, $f_{low}$ is calculated for each of the tests. Then, a test, in which a value of $f_{low}$ is less than the minimum $f_{upp}$, is selected. Therefore, only for the tests selected in a narrowing process, a p-value calculation process is conducted to acquire the minimum p-value by calculating the p-value.

If the test number $N_t$ is large, the calculation amount for $f_{low}$ and $f_{upp}$ is sufficiently less than that for the p-value. Accordingly, rather than calculating the p-value for each of all tests, the tests are narrowed down by calculating $f_{low}$ and $f_{upp}$ for each of the tests, and p-values are calculated only for the tests after the narrowing process, respectively. Hence, the multiple testing is performed at a higher speed. The calculation amount of the product of the p-value is $O((\chi-n)N_t)$; however, the calculation amount of a product of $f_{low}$ and $f_{upp}$ is $O(1)$ in the present invention.

Figure 6:
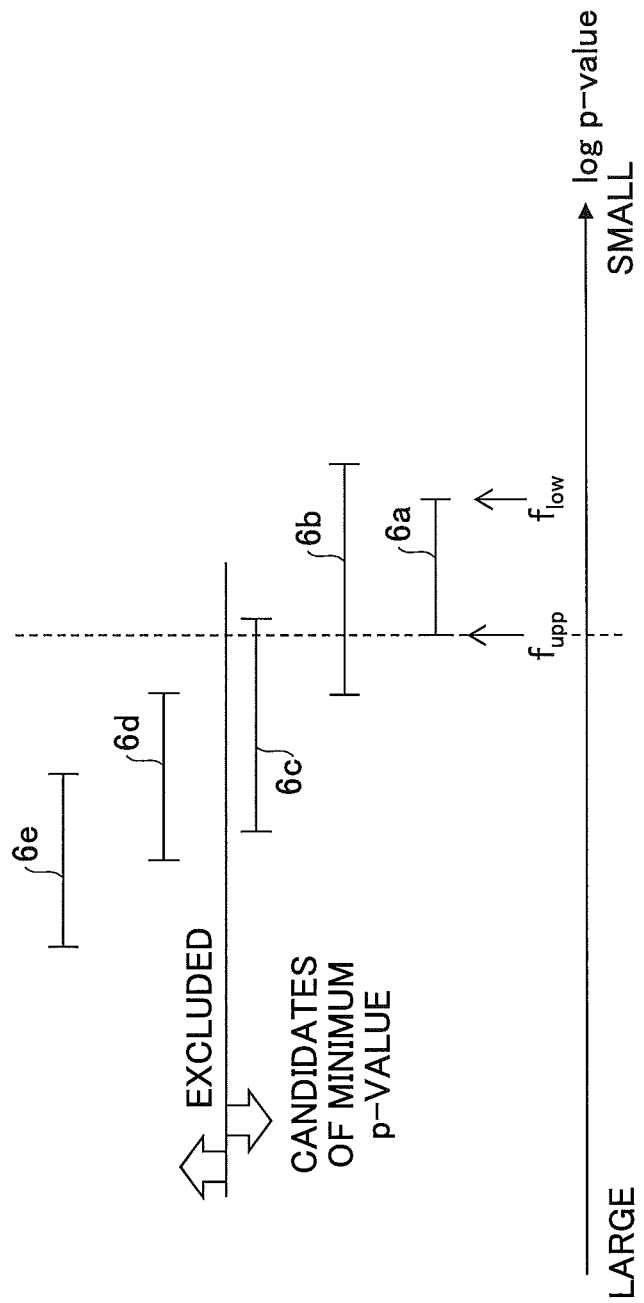
FIG. 6 is a diagram illustrating an example of a narrowing process in a present invention.

FIG. 6 is a diagram illustrating an example of the narrowing process in the present invention. In FIG. 6, a logarithm of the p-value is indicated on a horizontal axis, and the p-value becomes lesser from left to right. $f_{low}$ and $f_{upp}$ acquired for each of the tests are indicated. In this example, $f_{low}$ and $f_{upp}$, which are calculated for tests 6a, 6b, 6c, 6d, and 6e, are illustrated.

In the narrowing process, since the test 6a indicates the minimum $f_{upp}$ among all tests 6a through 6e, the tests 6b and 6c, each of which indicates a lower value of $f_{low}$ than the minimum $f_{upp}$ of the test 6a, are specified. In this example, the tests 6a through 6c are selected, and the tests 6d and 6e are excluded. In the embodiment, specifically, by acquiring the effective inequality (Formula 4) giving the lower limit of the p-value, a range of an appropriate p-value for each of a plurality of tests is acquired, and tests to be the candidates are precisely selected. Hence, it is possible to perform the p-value calculation process at higher speed.

Figure 7:
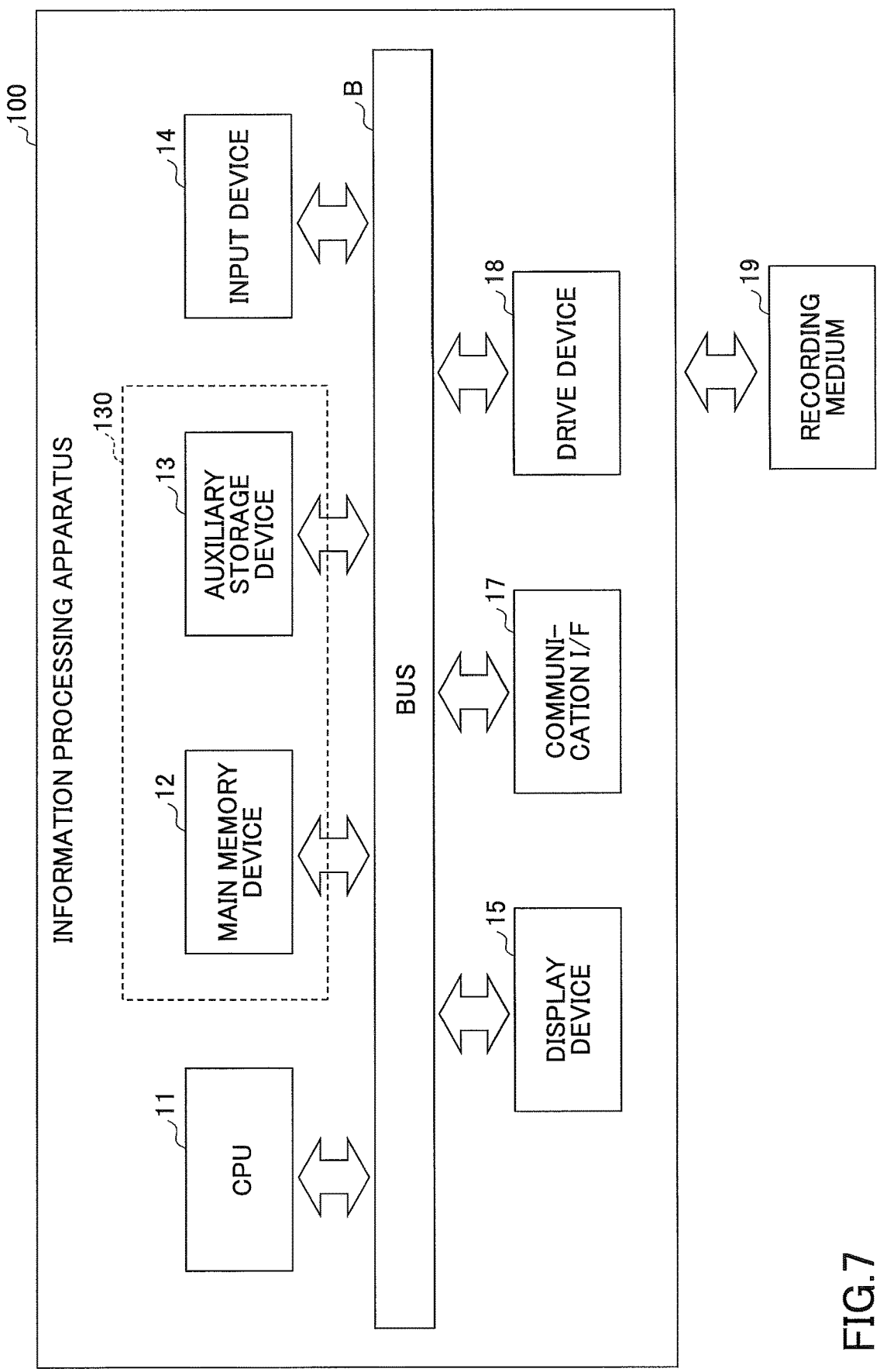
FIG. 7 is a diagram illustrating hardware configuration of an information processing apparatus.

An information processing apparatus 100 realizing the p-value calculation process according to the embodiment includes a hardware configuration as illustrated in FIG. 7. FIG. 7 is a diagram illustrating the hardware configuration of the information processing apparatus. In FIG. 7, the information processing apparatus 100 is an apparatus controlled by a computer, and includes a Central Processing Unit (CPU) 11, a main memory device 12, an auxiliary storage device 13, an input device 14, a display device 15, a communication InterFace (I/F) 17, and a drive device 18, which are connected through a bus B.

The CPU 11 corresponds to a processor to control the information processing apparatus 100 in accordance with a program stored in the main device 12. A Random Access Memory (RAM), a Read Only Memory (ROM), and/or the like may be used as the main device 12 to store or temporarily store the program to be executed by the CPU 11, data used for a process by the CPU 11, data acquired by the process of the CPU 11, and the like.

A Hard Disk Drive (HDD) or the like may be used as the auxiliary storage device 13 to store data such as programs for performing various processes. A part of a program stored in the auxiliary storage device 13 is loaded into the main memory device 12 and executed by the CPU 11, so that various processes are realized. A storage part 130 corresponds to one or more of the main storage device 12 and the auxiliary storage device 13.

The input device 14 includes a mouse, a keyboard, and the like, and is used for a user such as an analyst, or the like to input various information items used for a process conducted by the information processing apparatus 100. The display device 15 displays the various information items under control of the CPU 11. The input device 14 and the display device 15 may be a user interface such as an integrated touch panel. The communication I/F 17 conducts wired or wireless communications through a network. The communications conducted by the communication I/F 17 are not limited to wired or wireless communications.

A program realizing the p-value calculation process conducted by the information processing apparatus 100 may be provided to the information processing apparatus 100 by a recording medium 19 such as a Compact Disc Read-Only Memory (CD-ROM) or the like, for instance.

The drive device 18 interfaces between the recording medium 19 (which may be CD-ROM or the like) set into the drive device 18, and the information processing apparatus 100.

Also, the program realizing the p-value calculation process pertinent to an aspect of the embodiment, which will be described later, is stored in the recording medium 19. The program stored in the recording medium 19 is installed into the information processing apparatus 100 through the drive device 18. The installed program becomes possible to be executed by the information processing apparatus 100.

The recording medium 19 storing the program is not limited to a CD-ROM. The recording medium 19 may be any type of a recording medium, which is a non-transitory tangible computer-readable medium including a data structure. As the recording medium 19, a portable recording medium such as a Digital Versatile Disk (DVD), a Universal Serial Bus (USB) memory, or the like, or a semiconductor memory such as a flash memory may be used other than the CD-ROM.

Figure 8:
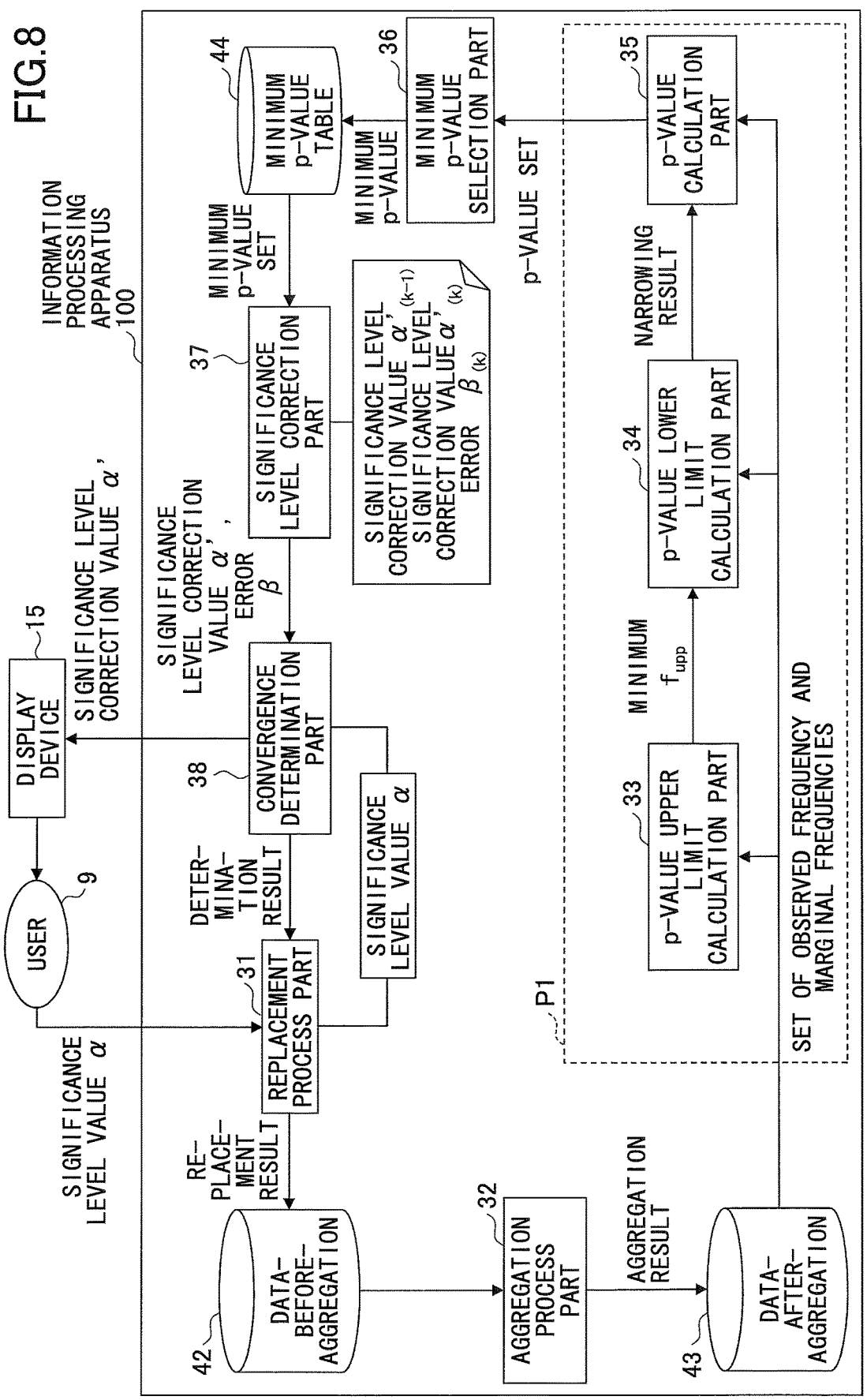
FIG. 8 is a diagram illustrating a first example of a functional configuration of the information processing apparatus in the embodiment.

FIG. 8 is a diagram illustrating a first example of a functional configuration of the information processing apparatus in the embodiment. In FIG. 8, the information processing apparatus 100 includes a replacement process part 31, an aggregation process part 32, a p-value upper limit calculation part 33, a p-value lower limit calculation part 34, a p-value calculation part 35, a minimum p-value selection part 36, a significance level correction part 37, and a convergence determination part 38.

The parts 31 through 38 are realized by respective processes, which the program installed into the information processing apparatus 100 causes the CPU 11 to perform.

Also, the storage part 130 stores data-before-aggregation 42, data-after-aggregation 43, a minimum p-value table 44, a significance level correction value $\alpha$, a significance level correction value $\alpha'_{(k)}$, a significance level correction value $\alpha'_{(k-1)}$, an error $\beta_{(k)}$, and the like.

The replacement process part 31 randomly rearranges the presence or absence of the specific event occurrence stored in the data-before-aggregation 42 (FIG. 9), which is stored in the storage part 130 (permutation). The data-before-aggregation 42 is replaced with a result from rearranging the presence or absence of the specific event occurrence (rearrangement result).

The aggregation process part 32 conducts the multiple testing as the data-before-aggregation 42 that has been permutated is used as an input. The aggregation process part 32 creates the cross tabulation table for each of the tests for the presence or absence of the specific event occurrence with respect to each of the attributes, acquires the observed frequency and the marginal frequencies from the cross tabulation table, and outputs and stores an aggregation result indicating the observed frequencies and the marginal frequencies into the data-after-aggregation 43 (FIG. 10) in the storage part 130. In this view, the data-after-aggregation 43 is regarded as an example of a multiple testing simultaneous aggregation table.

The p-value upper limit calculation part 33 acquires the observed frequency n and the marginal frequencies $\chi$, $N_c$, and $N_t$ from the data-after-aggregation 43, calculates the p-value upper limit ($f_{upp}$) for each of the tests, and selects a minimum value (minimum $f_{upp}$) from among multiple p-value upper limits ($f_{upp}$). The minimum $f_{upp}$ is reported to the p-value lower limit calculation part 34.

The p-value lower limit calculation part 34 acquires the observed frequency n and the marginal frequencies $\chi$, $N_c$, and $N_t$ from the data-after-aggregation 43, calculates the p-value lower limit ($f_{low}$) for each of the tests, and selects tests as the candidates (the test candidates) for the p-value calculation, which acquire p-value lower limits ($f_{low}$) less than the minimum value (minimum $f_{upp}$) among the p-value upper limits. A narrowing result indicating the test candidates is reported to the p-value calculation part 35.

The p-value calculation part 35 calculates a p-value using Formula 1 and Formula 2 with respect to each of the test candidates acquired by the p-value lower limit calculation part 34. A set of multiple p-values calculated by the p-value calculation part 35 is reported to the minimum p-value selection part 36.

The p-value upper limit calculation part 33, the p-value lower limit calculation part 34, and the p-value calculation part 35 correspond to an example of a narrowing part P1 for the narrowing process by an inequality (Formula 4), which will be described later. The narrowing process will be described with reference to FIG. 13.

The minimum p-value selection part 36 selects the minimum p-value from a set of the p-values reported from the p-value calculation part 35, and additionally stores the selected minimum p-value to the minimum p-value table 44 (FIG. 11).

The significance level correction part 37 updates the significance level correction value $\alpha'$ and the error $\beta$. The significance level correction part 37 acquires the set of the minimum p-values from the minimum p-value table 44, and sets, as the significance level correction value $\alpha'_{(k)}$, a greatest minimum p-value from the minimum p-values of top $(100 \times \alpha)\%$ or less in the set of the minimum p-value by using the significance level correction value $\alpha$ determined by a user 9 such as the analyst or the like.

Also, the significance level correction part 37 acquires a $k^{th}$ error $\beta_{(k)}$ based on the significance level correction value $\alpha'_{(k)}$ at a $k^{th}$ permutation and on the significance level correction value $\alpha'_{(k-1)}$ at a $(k-1)^{th}$ permutation, by calculating Formula 12:

$$\beta_{(k)} = \frac{|\tilde{\alpha}_{(k)} - \tilde{\alpha}_{(k-1)}|}{\tilde{\alpha}_{(k)}} \qquad \text{[Formula 12]}$$

The significance level correction part 37 sets a current significance level correction value $\alpha'_{(k)}$ to the significance level correction value $\alpha'_{(k-1)}$, and stores the acquired error $\beta_{(k)}$. In an initial state, the significance level correction value $\alpha'$ indicated by the user 9 is set to the significance level correction value $\alpha'_{(k-1)}$. Thus, the significance level correction value $\alpha'_{(k)}$ and the error $\beta_{(k)}$ are reported to the convergence determination part 38 as the significance level correction value $\alpha'$ and the error $\beta$.

Upon receiving the significance level correction value $\alpha'$ and the error $\beta$ from the significance level correction part 37, the convergence determination part 38 compares the error $\beta$ with a convergence determination value $\varepsilon$ defined beforehand. When the error $\beta$ is less than the convergence determination value $\varepsilon$, the convergence determination part 38 displays the significance level correction value $\alpha'$ as an acquired p-value on the display device 15, and terminates the p-value determination process according to the embodiment. When the error $\beta$ is greater than or equal to the convergence determination value $\varepsilon$, the convergence determination part 38 reports a determination result indicating a nonconvergence to the replacement process part 31. Upon receiving a determination result, the replacement process part 31 repeats the above described process.

Next, configuration examples of the data-before-aggregation 42, the data-after-aggregation 43, and the minimum p-value table 44 will be described.

FIG. 9 is a diagram illustrating a configuration example of the data-before-aggregation. In FIG. 9, the data-before-aggregation 42 corresponds to a table that cumulatively stores statistics data, and the like, and includes items of "ID", "PRESENCE OR ABSENCE OF SPECIFIC EVENT OCCURRENCE", "ATTRIBUTE_1", "ATTRIBUTE_2", . . . , "ATTRIBUTE_m", and the like.

The item "ID" indicates identification information specifying a record. The item "ID" may specify an individual such as a patient, a purchaser, or the like. The item "PRESENCE OR ABSENCE OF SPECIFIC EVENT OCCURRENCE" indicates development or non-development (case or control) of a specific disease, purchase or non-purchase of a specific product, or the like. In a case in which the specific disease is developed or the specific product is purchased, the item "PRESENCE OR ABSENCE OF SPECIFIC EVENT OCCURRENCE" indicates "1". In a case in which the specific product is not purchased, the item "PRESENCE OR ABSENCE OF SPECIFIC EVENT OCCURRENCE" indicates "0".

The items "ATTRIBUTE_1", the "ATTRIBUTE_2", . . . , and the "ATTRIBUTE_m" represent attributes pertinent to the relevance of the presence of absence of the specific event occurrence. When the attribute is in effect, a value of the attribute indicates "1". When the attribute is not in effect, the value of the attribute indicates "0". In a case concerning a specific disease, types of the multiple bases are represented by the items "ATTRIBUTE_1", the "ATTRIBUTE_2", . . . , and the "ATTRIBUTE_m". In case concerning a specific product, a region name, an age group, weather information, a time range, other names of products likely to be purchased together may be represented by the items "ATTRIBUTE_1", the "ATTRIBUTE_2", . . . , and the "ATTRIBUTE_m".

FIG. 10 is a diagram illustrating a configuration example of the data-after-aggregation. In FIG. 10, the data-after-aggregation 43 corresponds to a table that stores a value of the observed frequency and values of multiple marginal frequencies for each of the tests, and includes items of "OBSERVED FREQUENCY n", "MARGINAL FREQUENCY $\chi$", "MARGINAL FREQUENCY $N_e$", "MARGINAL FREQUENCY $N_t$", and the like. The data-after-aggregation 43 corresponds to the example of the multiple testing simultaneous aggregation table.

The item "OBSERVED FREQUENCY n" indicates a value of "n" in the cross tabulation table (FIG. 1) for each of the tests. The items of "MARGINAL FREQUENCY $\chi$", "MARGINAL FREQUENCY $N_c$", and "MARGINAL FREQUENCY $N_t$" indicate values of "$\chi$", "$N_c$", and "$N_t$", respectively.

FIG. 11 is a diagram illustrating a configuration example of the minimum p-value table. In FIG. 11, the minimum p-value table 44 corresponds to a table that cumulatively stores the minimum p-values selected by the minimum p-value selection part 36. For each iteration until the p-value calculation process is converged, the minimum p-values are accumulated in the minimum p-value table 44.

This example illustrates that "0.0004", "0.0006", "0.0007", and the like are accumulated in the minimum p-value table 44 due to iterations. It may be preferable that the minimum p-value acquired at every iteration is associated with a record of the set of the observed frequency and the marginal frequencies pertinent to the test having the acquired minimum p-value. Alternatively, it may be preferable to provide an item for storing the set of the observed frequency and the marginal frequencies in the minimum p-value table 44.

Figure 12:
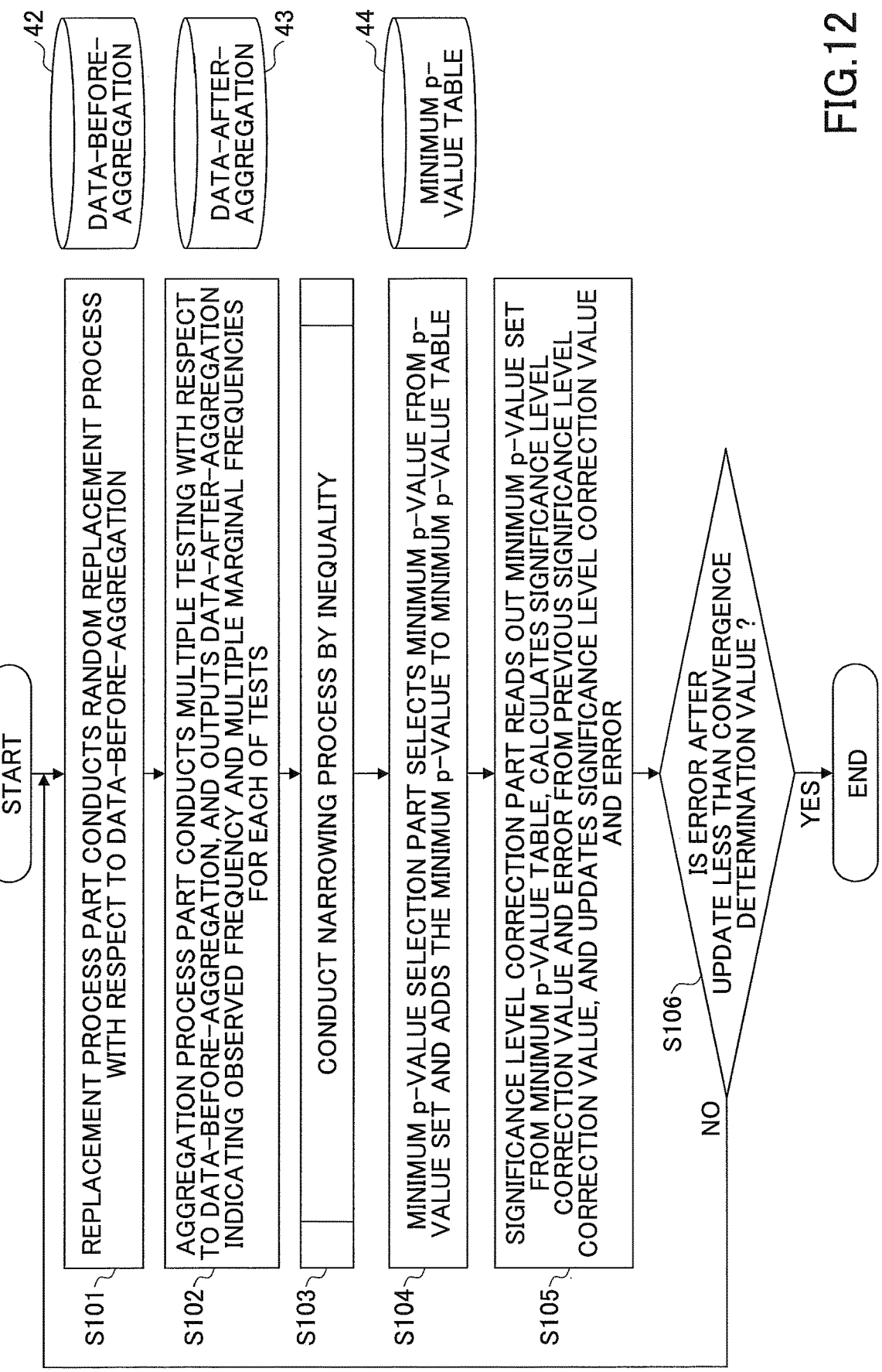
FIG. 12 is a flowchart for explaining a p-value calculation process in a first example of the functional configuration in FIG. 8.

FIG. 12 is a flowchart for explaining the p-value calculation process in the first example of the functional configuration in FIG. 8. In FIG. 12, when the significance level correction value $\alpha$ is acquired from the user 9 and is stored in the storage part 130; additionally, the replacement process part 31 randomly rearranges the presence or absence of the specific event occurrence in order to replace the data-before-aggregation 42 (step S101).

Next, the aggregation process part 32 conducts the multiple testing with respect to the data-before-aggregation 42, and outputs the data-after-aggregation 43 indicating the observed frequency and the multiple marginal frequencies for each of the tests (step S102).

When the data-after-aggregation 43 is output to the storage part 130, the narrowing process is conducted by the inequality (Formula 4) by the narrowing part P1 (step S103). The narrowing process in accordance with the inequality (Formula 4) will be described with reference to FIG. 13. When the tests to be subject for the p-value calculation process are narrowed down, a set of p-values of respective test candidates is acquired.

The minimum p-value selection part 36 selects the minimum p-value from the set of the p-values and adds the selected minimum p-value to the minimum p-value table 44 (step S104).

When the minimum p-value is added to the minimum p-value table 44, the significance level correction part 37 reads out the set of the minimum p-values from the minimum p-value table 44, and calculates the significance level correction value $\alpha'$ at a current iteration. Also, the significance level correction part 37 calculates the error $\beta$ with respect to a previous significance level correction value, and updates the significance level correction value $\alpha'$ and the error $\beta$ (step S105).

The significance level correction part 37 reads out the significant level a indicated by the user 9, which is stored in the storage part 130, and specifies the greatest minimum p-value from the minimum p-values of top (100×$\alpha$)% or less in the set of the minimum p-values. The significance level correction part 37 sets the specified minimum p-value to a current significance level correction value $\alpha'$.

The significance level correction value, which was previously stored as $\alpha'_{(k)}$ in the storage part 130, is stored as the significance level correction value $\alpha'_{(k-1)}$, and the error $\beta_{(k)}$ is calculated between the current significance level correction value $\alpha'$ and the previous significance level correction value $\alpha'_{(k-1)}$. The significance level correction part 37 stores the significance level correction value $\alpha'$ and the error $\beta_{(k)}$, as currently calculated, to update the significance level correction value $\alpha'_{(k)}$ and the error $\beta_{(k)}$ being stored in the storage part 130. Also, the significance level correction part 37 reports the significance level correction value $\alpha'$ and the error $\beta_{(k)}$, as currently calculated, to the convergence determination part 38.

In response to a report from the significance level correction part 37, the convergence determination part 38 determines whether the error $\beta_{(k)}$ is less than the convergence determination value $\varepsilon$ (step S106). By the convergence determination part 38, when it is determined that the error $\beta_{(k)}$ is greater than or equal to the convergence determination value $\varepsilon$ (NO of step S106), the p-value calculation process goes back to step S101, and repeats from a random replacement process. However, by the convergence determination part 38, when it is determined that the error $\beta_{(k)}$ is less than the convergence determination value ε (YES of step S106), the p-value calculation process is terminated.

Figure 13:
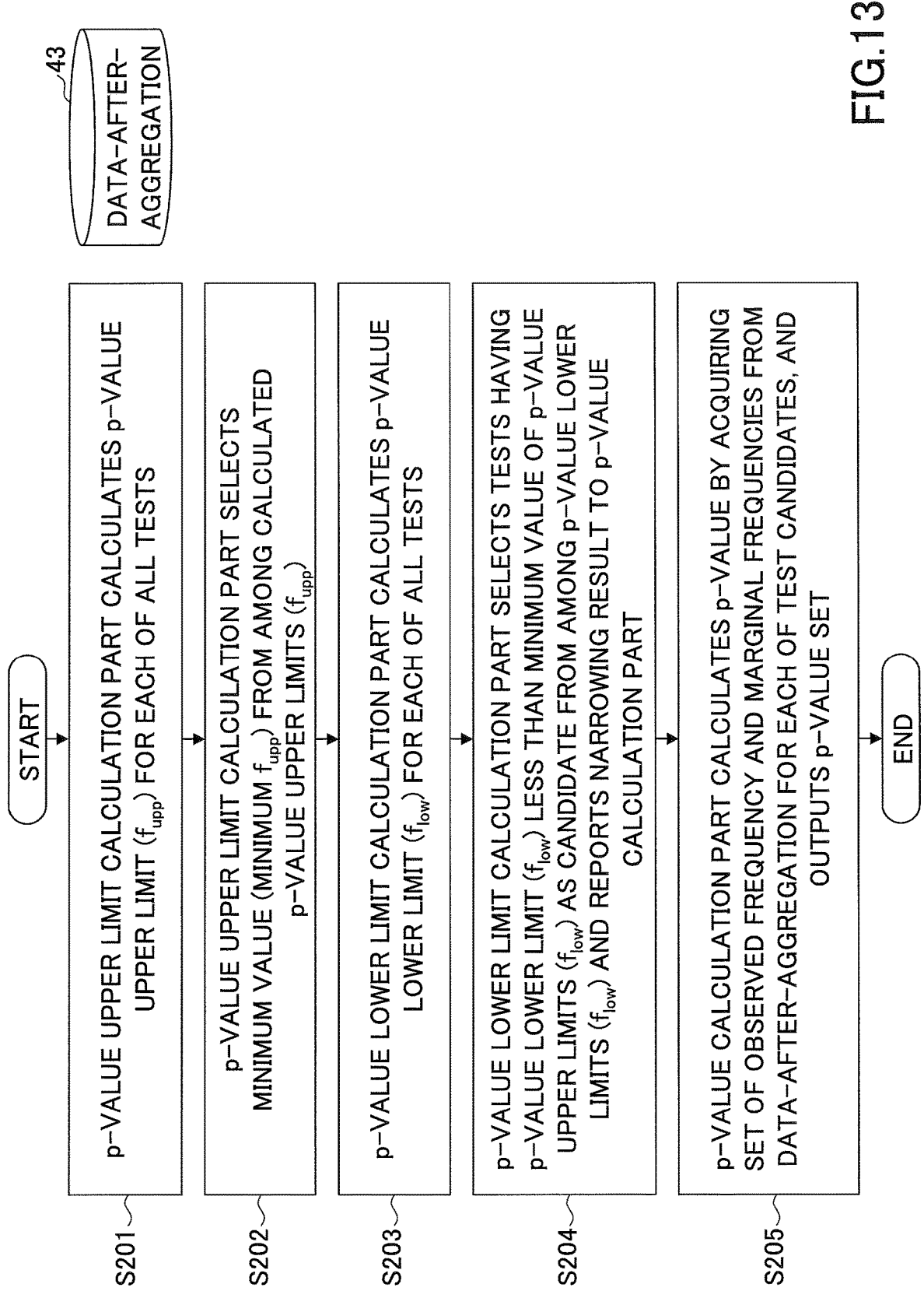
FIG. 13 is a flowchart for explaining a narrowing process in accordance with an inequality in step S103 in FIG. 12.

FIG. 13 is a flowchart for explaining the narrowing process in accordance with the inequality in step S103 in FIG. 12. In FIG. 13, the p-value upper limit calculation part 33 calculates the p-value upper limit ($f_{upp}$) for each of all tests (step S201). The p-value upper limit calculation part 33 acquires the set of the observed frequency and the marginal frequencies from each of records of the data-after-aggregation 43, and calculates the p-value upper limit ($f_{upp}$) for each of the tests.

Thus, the p-value upper limit calculation part 33 selects a minimum value (minimum $f_{upp}$) from among multiple p-value upper limits ($f_{upp}$) calculated in step S201 (step S202). The minimum value (minimum $f_{upp}$) selected from the multiple p-value upper limits ($f_{upp}$) is reported to the p-value lower limit calculation part 34.

The p-value lower limit calculation part 34 calculates a p-value lower limit ($f_{low}$) for each of all tests (step S203). The p-value lower limit calculation part 34 acquires the set of the observed frequency and the marginal frequencies from each of records of the data-after-aggregation 43, and calculates the p-value lower limit ($f_{low}$) for each of the tests.

Next, the p-value lower limit calculation part 34 selects one or more tests as candidates (test candidates) having p-value lower limits ($f_{low}$) less than the minimum value (minimum $f_{upp}$) among the multiple p-value upper limits ($f_{upp}$), and reports a narrowing result to the p-value calculation part 35 (step S204). The narrowing result indicates the set of the observed frequency and the marginal frequencies for each of the test candidates.

The p-value calculation part 35 calculates the p-value by acquiring the set of the observed frequency and the marginal frequencies for each of the test candidates from the data-after-aggregation 43, and outputs a set of the p-values (step S205). Then, the narrowing process in accordance with the inequality is terminated.

In the example of the functional configuration in FIG. 8, the tests having the p-value lower limits ($f_{low}$) less than the minimum value among the multiple p-value upper limits ($f_{upp}$) are selected as the test candidates; however, it may be considered, in calculating the p-value for the test with the minimum value among the multiple p-value upper limits ($f_{upp}$), to select a test as a candidate in the case of having a p-value lower limit ($f_{low}$) further less than the acquired p-value. An example of a functional configuration for a p-value calculation method for this case will be described below.

FIG. 14 is a diagram illustrating a second example of the functional configuration of the information processing apparatus in the embodiment. In FIG. 14, the information processing apparatus 100 includes a replacement process part 31, an aggregation process part 32, a p-value upper limit calculation part 33, a p-value calculation part 54, a p-value lower limit calculation part 55, a minimum p-value selection part 36, a significance level correction part 37, and a convergence determination part 38.

The parts 31 through 33, 54, 55, 36, and 37 are realized by respective processes, which a program installed into the information processing apparatus 100 causes the CPU 11 to perform.

Also, the storage part 130 stores data-before-aggregation 42, data-after-aggregation 43, a minimum p-value table 44, a significance level correction value α, a significance level correction value α'$_{(k)}$, a significance level correction value α'$_{(k-1)}$, an error β$_{(k)}$, and the like.

The replacement process part 31 randomly rearranges a presence or absence of the specific event occurrence stored in the data-before-aggregation 42 (FIG. 9), which is stored in the storage part 130 (permutation). The data-before-aggregation 42 is replaced with a rearrangement result.

The aggregation process part 32 conducts the multiple testing as the rearranged data-before-aggregation 42 is set as an input. The aggregation process part 32 creates the cross tabulation table for each of the tests for the presence or absence of the specific event occurrence with respect to each of the attributes, acquires the observed frequency and the marginal frequencies from the cross tabulation table, and outputs and stores an aggregation result indicating the observed frequencies and the marginal frequencies into the data-after-aggregation 43 (FIG. 10) in the storage part 130.

The p-value upper limit calculation part 33 acquires the observed frequency n and the marginal frequencies χ, N$_c$, and N$_t$ from the data-after-aggregation 43, calculates the p-value upper limit ($f_{upp}$) for each of the tests, and selects a minimum value (minimum $f_{upp}$) from among multiple p-value upper limits ($f_{upp}$). The minimum $f_{upp}$ reports to the p-value calculation part 54.

Upon receiving the report of the minimum $f_{upp}$ from the p-value upper limit calculation part 33, the p-value calculation part 54 acquires the observed frequency n and the marginal frequencies χ, N$_c$, and N$_t$ from the data-after-aggregation 43, calculates the p-value, and sets the p-value as a p-value threshold. The p-value calculation part 54 calls a function of the p-value lower limit calculation part 55 to narrow down the test candidates by using the calculated p-value threshold.

When acquiring the test candidates as return values from the p-value lower limit calculation part 55, the p-value calculation part 54 calculates the p-value for each of the tests, and reports a set of multiple p-values acquired from the calculation to the minimum p-value selection part 36.

The p-value lower limit calculation part 55 acquires the observed frequency n and the marginal frequencies χ, N$_c$, and N$_t$ from the data-after-aggregation 43, calculates a p-value lower limit ($f_{low}$) for each of all tests, and selects from among multiple p-value lower limits ($f_{low}$) respective to all tests, as candidates, tests having the p-value lower limits ($f_{low}$) less than the p-value threshold reported from the p-value calculation part 54. The p-value lower limit calculation part 55 reports the selected test candidates as returned values to the p-value calculation part 54.

The p-value upper limit calculation part 33, the p-value calculation part 54, and the p-value lower limit calculation part 55 correspond to an example of a narrowing part P2 that conducts a narrowing process using the inequality (Formula 4). This narrowing process will be described later.

The minimum p-value selection part 36 selects the minimum p-value from the set of the p-values reported from the p-value calculation part 54, and additionally stores the selected minimum p-value to the minimum p-value table 44 (FIG. 11).

The significance level correction part 37 updates the significance level correction value α' and the error R. The significance level correction part 37 acquires the set of the minimum p-value from the minimum p-value table 44, and sets, as the significance level correction value α'$_{(k)}$, a greatest minimum p-value from the minimum p-values of top (100×α)% or less in the set of the minimum p-values by using the significance level correction value α determined by the user 9.

Also, the significance level correction part 37 calculates the error β$_{(k)}$ at a k$^{th}$ time by the above described Formula 12 from the significance level correction value $\alpha'_{(k)}$ at a $k^{th}$ permutation time and the significance level correction value $\alpha'_{(k-1)}$ at a $(k-1)^{th}$ permutation time.

In the storage part 130, the significance level correction part 37 sets the significance level correction value $\alpha'_{(k)}$ currently being stored to the significance level correction value $\alpha'_{(k-1)}$, and stores a currently acquired error $\beta_{(k)}$. The significance level correction value $\alpha'$ indicated by the user 9 in the initial state becomes is set to the significance level correction value $\alpha'_{(k-1)}$. Thus, the significance level correction value $\alpha'_{(k)}$ and the error $\beta_{(k)}$ are reported to the convergence determination part 38 as the significance level correction value $\alpha'$ and the error $\beta$.

Upon receiving the significance level correction value $\alpha'$ and the error $\beta$ from the significance level correction part 37, the convergence determination part 38 compares the error $\beta$ with a convergence determination value $\varepsilon$ defined beforehand. When the error $\beta$ is less than the convergence determination value $\varepsilon$, the convergence determination part 38 displays the significance level correction value $\alpha'$ as an acquired p-value on the display device 15, and terminates the p-value determination process according to the embodiment. When the error $\beta$ is greater than or equal to the convergence determination value $\varepsilon$, the convergence determination part 38 reports a determination result indicating a nonconvergence to the replacement process part 31. Upon receiving a determination result, the replacement process part 31 repeats the above described process.

Configuration examples of the data-before-aggregation 42, the data-after-aggregation 43, and the minimum p-value table 44 are similar to those in the first example of the functional configuration, and explanations thereof will be omitted. Moreover, parts other than the narrowing part P2 are similar to those in the first example of the functional configuration, and thus, the entire flowchart is similar to that depicted in FIG. 12. Hence, in the second example of the functional configuration, a flowchart pertinent to the narrowing part P2 will be described below.

FIG. 15 is a flowchart for explaining the narrowing process using the inequality in the second example of the functional configuration in FIG. 14. In FIG. 15, the p-value upper limit calculation part 33 calculates the p-value upper limit ($f_{upp}$) for each of all tests (step S401). For each of all tests, the p-value upper limit calculation part 33 acquires a set of the observed frequency and the marginal frequencies from the cross tabulation table, and calculates the p-value upper limit ($f_{upp}$).

Next, the p-value upper limit calculation part 33 selects a minimum value from among multiple p-value upper limits ($f_{upp}$) calculated in step S402. The selected minimum value (minimum $f_{upp}$) among the multiple p-value upper limits ($f_{upp}$) is reported to the p-value calculation part 54.

The p-value calculation part 54 acquires the set of the observed frequency and the marginal frequencies of a test having the minimum value (minimum $f_{upp}$) reported from the p-value upper limit calculation part 33, and acquires the p-value threshold by calculating the p-value (step S403). The p-value threshold is reported to the p-value lower limit calculation part 55.

The p-value lower limit calculation part 55 calculates the p-value lower limits ($f_{low}$) for each of the tests (step S404). The p-value lower limit calculation part 55 acquires the sets of the observed frequency and the marginal frequencies from each of records of the data-after-aggregation 43, and calculates multiple p-value lower limits ($f_{low}$) respectively for all tests.

Next, the p-value lower limit calculation part 55 selects tests having p-value lower limits ($f_{low}$) less than the p-value threshold from among the multiple p-value lower limits ($f_{low}$), and reports a narrowing result to the p-value calculation part 54 (step S405).

The p-value calculation part 54 calculates the p-value for each of the tests indicated by the narrowing result, and outputs a set of the p-values (step S406). Then, the narrowing process using the inequality is terminated.

As described above, according to the embodiment, by narrowing down the tests using the p-value upper limits ($f_{upp}$) and the p-value lower limits ($f_{low}$), it is possible to automatically set a threshold for narrowing down the tests independently of an experience of the analyst. Accordingly, it is possible for anyone, who analyzes the significant level $\alpha$ for the multiple testing, to reduce a calculation cost, regardless of a skill level of the analyst.

By narrowing down the tests using the p-value upper limits ($f_{upp}$) and the p-value lower limits ($f_{low}$), it is possible to acquire the minimum p-value with certainty. Accordingly, it is possible to acquire the significance level correction value $\alpha'$ at high speed without accuracy deterioration.

Also, in a case of comparing with a method using the Odds Ratio (OR), since a method for determining the p-value threshold depends on experience of the user 9 as the analyst, it is difficult to improve accuracy of the p-value threshold and to realize a high speed process. Moreover, there may be a case in which an accurate minimum p-value is not likely obtained in the method using the Odds Ratio (OR).

The calculation amount for acquiring an upper limit and a lower limit of the p-values is significantly less than that in a case of calculating the probability (the p-value) of the false positive for each of the tests. In the embodiment, since tests subject to a p-value calculation are narrowed down, it is possible to reduce the calculation amount. In a case of conducting the multiple testing in a genome analysis or the like, bases subject to the p-value calculation are narrowed down, and thus, the calculation amount is reduced.

As described above, in each of simulations of the permutation method, the data-after-aggregation 43 is created to include the observed frequency n and the marginal frequencies $\chi$, $N_c$, and $N_r$. By performing the narrowing process using the inequality (Formula 4) with respect to the data-after-aggregation 43, variable combinations (n, $\chi$, $N_c$, $N_r$) to be candidates one of which is likely to have the minimum p-value are narrowed down. A variable combination (n, $\chi$, $N_c$, $N_r$) represents arguments for each of the tests. With respect to the narrowed variable combinations (n, $\chi$, $N_c$, $N_r$), that is, the tests subject to the p-value calculation, the p-values are calculated, and the minimum p-value is selected from among the p-values.

By the above described method, in the embodiment, since the p-values are calculated only for the narrowed tests, it is possible to reduce the calculation cost more than in a case of calculating the p-values for all tests. Moreover, as the tests are narrowed down without fixing the marginal frequencies $N_c$ and $N_r$, even in a case in which the data-after-aggregation 43 contains missing values, which are not supported by a related art, it is possible to obtain the effect.

In the embodiment, it is possible to reduce an amount of calculating the probability of the false positive in the multiple testing.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An information processing apparatus, comprising:
a memory; and
a processor coupled to the memory and configured to
read, from a storage device, data-after-aggregation pertinent to a presence or absence of a specific event occurrence acquired by a multiple testing;
acquire an upper limit and a lower limit of a probability of a false positive for each of multiple tests based on the read data-after-aggregation;
set a value from multiple upper limits being acquired;
calculate the probability of the false positive with respect to each of tests having lower limits less than the value so that a calculation amount for calculating the probability of the false positive is reduced without degrading an accuracy of the multiple testing;
acquire a set of probabilities of the false positive;
obtain a probability value from the set of probabilities of the false positive; and
display the probability value on a display device.

2. The information processing apparatus as claimed in claim 1, wherein the processor is further configured to:
calculate the upper limit of the probability of the false positive for each of the multiple tests, and acquire a minimum value from the multiple upper limits being acquired, in order to set the value;
calculate the lower limit of the probability of the false positive for each of the multiple tests, and select the lower limits less than the value from among the multiple upper limits; and
calculate the probability of the false positive with respect to each of the tests and having the lower limits less than the value, the lower limits being selected.

3. The information processing apparatus as claimed in claim 1, wherein the processor is further configured to:
calculate the upper limit of the probability of the false positive for each of the tests so as to acquire the multiple upper limits for the tests, respectively, and acquire a minimum value from the multiple upper limits;
calculate the probability of the false positive of a test having the acquired minimum value, and set the calculated probability to the value; and
calculate multiple lower limits of the probability of the false positive, respectively for the multiple tests, and select the tests having the lower limits less than the value, to which the calculated probability is set, from among the multiple lower limits.

4. The information processing apparatus as claimed in claim 1, wherein the processor is further configured to:
perform a replacement process of the presence or absence of the specific event occurrence of data-before-aggregation, which indicates the presence or absence of the specific event occurrence and values of multiple attributes pertinent to relevance of the presence of absence of the specific event occurrence; and
create the data-after-aggregation indicating an aggregation result acquired by the multiple testing based on the data-before-aggregation, in which the presence or absence of the specific event occurrence is randomly replaced.

5. The information processing apparatus as claimed in claim 4, wherein the processor is further configured to
select a minimum probability of the false positive as a target to calculate a significant level correction value from the acquired set of probabilities of the false positive, and additionally store the minimum probability of the false positive in the memory;
calculate the significant level correction value by using the minimum probability of the false positive being stored in the memory; and
conduct the replacement process until the significant level correction value is converged.

6. A non-transitory computer-readable recording medium storing an information processing program for causing a computer to perform a process comprising:
reading, from a storage device, data-after-aggregation pertinent to a presence or absence of a specific event occurrence acquired by a multiple testing;
acquiring an upper limit and a lower limit of a probability of a false positive for each of multiple tests based on the read data-after-aggregation;
setting a value from multiple upper limits being acquired;
calculating the probability of the false positive with respect to each of tests having lower limits less than the value so that a calculation amount for calculating the probability of the false positive is reduced without degrading an accuracy of the multiple testing;
acquiring a set of probabilities of the false positive;
obtaining a probability value from the set of probabilities of the false positive; and
displaying the probability value on a display device.

7. An information processing method by a computer, comprising:
reading, from a storage device, data-after-aggregation pertinent to a presence or absence of a specific event occurrence acquired by a multiple testing;
acquiring an upper limit and a lower limit of a probability of a false positive for each of multiple tests based on the read data-after-aggregation;
setting a value from multiple upper limits being acquired;
calculating the probability of the false positive with respect to each of tests having lower limits less than the value so that a calculation amount for calculating the probability of the false positive is reduced without degrading an accuracy of the multiple testing; and
acquiring a set of probabilities of the false positive;
obtaining a probability value from the set of probabilities of the false positive; and
displaying the probability value on a display device.

* * * * *